(12) United States Patent
Matthias et al.

US008142719B2

(10) Patent No.: US 8,142,719 B2
(45) Date of Patent: Mar. 27, 2012

(54) ANALYSIS DEVICE

(75) Inventors: Torsten Matthias, Wendelsheim (DE);
Hugo Ribeiro, Mainz (DE); Hans-Peter Schimon, Heiningen (DE); Peter Van Praet, Haasrode (BE)

(73) Assignee: Torsten Matthias, Wendelsheim (DE)

( * ) Notice: Subject to any disclaimer, the term of this patent is extended or adjusted under 35 U.S.C. 154(b) by 810 days.

(21) Appl. No.: 12/291,375

(22) Filed: Nov. 7, 2008

(65) Prior Publication Data

US 2009/0280572 A1    Nov. 12, 2009

(30) Foreign Application Priority Data

May 12, 2008  (DE) .................. 10 2008 022 835

(51) Int. Cl.
*G01N 21/00*    (2006.01)
*B01J 19/00*    (2006.01)
(52) U.S. Cl. .......... 422/64; 422/500; 422/501; 422/509; 422/521; 436/43; 436/45; 436/49
(58) Field of Classification Search .............. 422/64, 422/500, 501, 509, 521; 436/43, 45, 49
See application file for complete search history.

(56) References Cited

U.S. PATENT DOCUMENTS

| 5,084,242 | A | | 1/1992 | Sakuma | |
|---|---|---|---|---|---|
| 6,146,594 | A | * | 11/2000 | De Graaff et al. | 422/501 |
| 6,338,825 | B1 | * | 1/2002 | Skeen | 422/526 |
| 6,756,232 | B1 | * | 6/2004 | Schermer et al. | 436/180 |
| 7,575,937 | B2 | * | 8/2009 | Wiggli et al. | 436/180 |

FOREIGN PATENT DOCUMENTS

| CH | 696 030 A5 | 11/2006 |
|---|---|---|
| DE | 101 16 642 C1 | 12/2002 |
| DE | 10 2007 018 483 A1 | 10/2007 |
| EP | 0 725 267 A2 | 8/1996 |
| EP | 1 206 967 A2 | 5/2002 |
| EP | 1 477 815 A1 | 11/2004 |
| EP | 1 829 613 A1 | 9/2007 |
| JP | 64-006760 A | 1/1989 |
| WO | WO 02/059626 A1 | 8/2002 |
| WO | WO 2005/103725 A1 | 11/2005 |
| WO | WO 2006/000115 A1 | 1/2006 |
| WO | WO 2007/071613 A1 | 6/2007 |

* cited by examiner

*Primary Examiner* — Jill Warden
*Assistant Examiner* — Dwan A Gerido
(74) *Attorney, Agent, or Firm* — Hudak, Shunk & Farine Co. LPA

(57) ABSTRACT

A device is disclosed, being an analysis device for the study of biological or chemical samples by means of a reagent liquid supplied via a pipette. The device has an instrument housing with a base plate, a working plate arranged on the base plate horizontally to receive the samples in a sample holder having several wells, a robot manipulator arranged above the working plate, which carries a horizontal support arm with a slide. A needle system is fastened to the slide and can move in the Z direction, carrying 3 needles and being brought into vertical positions by a first vertical drive. The needle tips can be placed in an upper position above and in a lower position below a well. The middle needle can move vertically relative to the other two needles, which can be raised and lowered by a second vertical drive. The horizontal spacing of the three needles is so small that all three needles can be positioned with their tips inside the same wells. In particular, the working plate is mounted on the base plate so that it can turn.

17 Claims, 15 Drawing Sheets

ANALYSIS DEVICE

FIELD OF INVENTION

Figure 1:
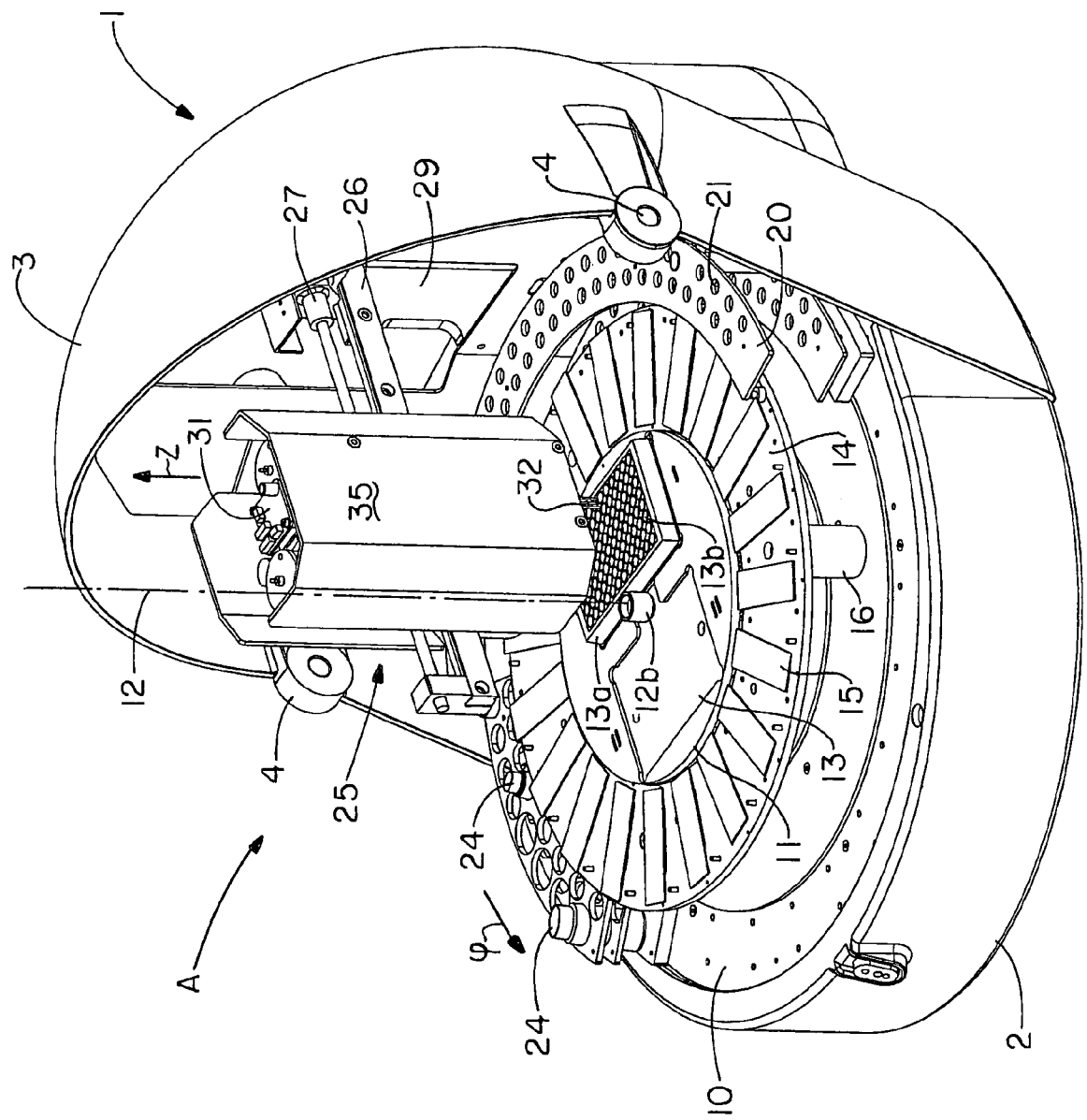

The invention concerns a device, especially an analysis device, and a system for the study of biological or chemical samples by means of a reagent liquid supplied via a pipette, as well as a method for the study of biological or chemical samples by means of a reagent liquid supplied via a pipette, wherein the samples are each held in sample holders that are arranged on the work platform.

BACKGROUND OF THE INVENTION

From publication WO 2006/000115 A1 is known a device and a method for the arranging of pipette or dispenser tips in a system for manipulating of liquid samples. Such a device comprises a robot manipulator for the orienting of pipette or dispenser tips in an X direction and in a Y direction running essentially perpendicular to the former, with respect to sample holders arranged in or on the system. Such devices furthermore comprise pipette or dispenser tips, which extend essentially vertically and which can be raised and lowered in a Z direction running essentially perpendicular to the X and Y directions. Furthermore, such devices comprise drive units for moving the robot manipulator and processors for controlling the movements and actions of the robot manipulator or the pipette or dispenser tips. Corresponding devices and systems are known for use in the study of genes (genomics), proteins (proteomics), for the discovery of new active substances (drug discovery) and in clinical diagnostics, such as the work platform marketed by the firm Tecan Trading AG, Seestrasse 103, CH-8708 Männerdorf under the name "Genesis Robotic Sample Processor". This is a device for the manipulating of samples in containers and/or on specimen slides, wherein the containers and/or specimen slides are arranged on an essentially horizontal working field with a lengthwise dimension X and a transverse dimension Y and wherein the device contains robot manipulators for manipulating the samples. This manipulating can involve the taking up and/or giving out of liquids, e.g., within this X-Y field. Moreover, centrifuges and other processing stations or analysis stations can be provided, such as fluorescence readers and the like. For such work platforms it is also important to identify objects, such as test tubes, microtitration plates, and other containers holding specimens by means of a corresponding detection device, such as a barcode reader or the like: such known work platforms preferably have, for purposes of liquid handling, a robot manipulator with an arm extending in the Y direction and at least one rail extending in the X direction, on which the arm is fastened and can move back and forth in the X direction; these extend basically vertically and can be raised and lowered in the Z direction, extending basically perpendicular to the work field; and there are drive units to move the robot manipulator and processors to control the movements and actions of the robot manipulator and/or pipette tips. Furthermore, liquid samples that are being processed or studied are usually found in tubes or in the wells of microtitration plates. Such tubes are placed in suitable holders, so that each holder can accommodate a row of tubes, which are thus arranged in a line alongside each other in the Y direction, i.e., the direction of the transverse dimension of the work platform. These holders can preferably be moved on the work table. Liquid samples can also be found in the wells of microtitration plates, or be transferred by pipette from the test tubes to these wells. Usually three microtitration plates are arranged on a so-called "carrier", which preferably can also move along the work table.

Furthermore, from publication CH 696 030 A5 there is known such a device for the manipulating of samples in containers and/or on specimen slides in the region of an X-Y field, wherein the first and the second robot manipulator can work at least the entire region of the X-Y field, practically without hindering each other. The ranges of action of the two robot manipulators can be chosen arbitrarily. The second robot manipulator, loaded with objects or not, can pass by the first robot manipulator. The moving around of various objects with the second robot manipulator, such as the shifting of active devices in the form of scanners (1D, 2D), cameras, print heads, etc., makes it possible to use the functions of this device over the entire field of the work platform. These active devices can be picked up with the second robot manipulator, even from outside the field, or be temporarily set down there. Thanks to an additional extensibility feature of the second robot manipulator, one can also service levels underneath the actual work field. Since the transporting of objects and the liquid handling are jobs that often do not take place at the same time, two independent robot manipulators are proposed.

From publication EP 1 829 613 A1 there is disclosed a storage unit for biological samples, with an essentially horizontal main standing surface and several storage chambers. In biological laboratories, especially in the laboratories of pathology institutes of universities or hospitals, biological samples such as tissue samples obtained from biopsy are very often kept as pieces of tissue in holders or as thin sections on glass specimen slides. A selection of such holders and glass specimen slides is offered, e.g., by the firm Thermo Shandon. In pharmaceutical research, chemical or biochemical compounds are routinely tested for their potential pharmaceutical activity. For this purpose, a large number of samples must be prepared in the shortest of time. Therefore, in pharmaceutical research laboratories one uses so-called "microtubes", which contain a sufficient amount of a particular substance. In order to cope as economically as possible with the huge numbers of such microtubes, these are packed in so-called "microtube cluster racks". For a robotized handling, it is especially preferable to use such racks as have a standing surface corresponding to the so-called "foot print" of a microtitration plate in the SBS standard (SBS=Society for Biomolecular Screening) and which is therefore often called an "SBS footprint". In the meantime, this standard has been standardized as ANSI/SBS 1-2004 by the ANSI (American National Standards Institute). Microtube cluster racks with 96 or 384 microtubes are known, for example, by the commercial name REMP Tube Technology™. On the other hand, thin sections of fixed specimens, such as those embedded in paraffin, are routinely placed on glass slides and viewed by means of light microscope in pathology.

Moreover, from publication WO 2005/103725 A1 there is known a device for the transporting or studying of liquids in a system for working with liquid samples. Such systems include, for example, a work field extending basically horizontally in an X direction and in a Y direction at right angles to it. The device contains at least one functional element with at least one functional end, while the functional elements are oriented basically perpendicular to the work field in a Z direction. The device includes at least one tilt unit for the tiltable holding of the at least one functional element. Such a system contains at least one robot arm, on which at least one such device is fastened. Such a robot arm is then configured to move the functional element in at least a partial region of the work field and at least in the Z direction. In the technical field of liquid handling, devices for the taking up and giving out of liquid samples are known as pipettes or pipetting devices.

Devices which can only be used for the giving out of liquid samples are usually called dispensers. In order to automate the pipetting process for volumes under 10 μl, one must distinguish two processes: defined taking up (aspiration) and the subsequent giving out (dispensing) of liquid samples. The pipette tip is usually moved between these two processes by the experimenter or an automatic machine, so that the place of taking up a liquid sample is often different from the place of giving it out. For a proper and reproducible taking up and/or giving out of a liquid, only the system which consists of pump (e.g., a diluter configured as a syringe pump), liquid line, and end piece (pipette tip) is significant. The giving out of a liquid with a pipette tip can occur from air or by touching of a surface. This surface can be the solid surface of a vessel into which the liquid sample is to be dispensed ("on tip touch"). It can also be the surface of a liquid located in this vessel ("on liquid surface"). A mixing process following the dispensing is recommended—especially for very small sample volumes in the nanoliter or even picoliter range—so that a uniform distribution of the sample volume in a reaction liquid is assured. From publication DE 101 16 642 C1 there is known a device with which liquids can be given out into the wells of a microtitration plate or pipetted from such containers. Work platforms or systems for the handling of liquids, such as the pipetting of liquids from containers, are known, e.g., from publication U.S. Pat. No. 5,084,242, which also proposes a tilting unit for the tiltable holding of the at least one pipetting device dispensing the liquid.

The publication DE 10 2007 018 483 A1 describes work platforms for the handling of liquids, such as the pipetting of liquids from containers and the distributing of same in the wells of a microtitration plate, which are known as "pipetting device" from publication WO 02/059626 A1 and as "device for precise docking at microplate wells" from publication EP 1 477 815 A1. It involves preferably work platforms for which a pipette tip, for example, can be automatically positioned at a certain spot. In particular, publication EP 1 477 815 A1 discloses an especially precise positioning of objects relative to the 1536 wells of a microtitration plate, so that one can avoid damaging a pipette tip, a temperature sensor, a pH probe, or another long and thin object which is supposed to be positioned in a well due to striking against the walls of the well or the surface of the microtitration plate. Furthermore, one can in this way practically rule out losses of sample and contamination of neighboring samples and of the work area. A precise docking at the wells with no danger of an unintentional touching of parts of the microtitration plate is therefore a fundamental requirement for routine working with a liquid handling system which can be used, e.g., for the automatic study of blood samples. A precise docking should be assured not only in the essentially horizontal plane of a Cartesian system of coordinates, defined by the X and Y directions; it should also be possible to position as precisely and reproducibly as possible the Z or height position of a functional tip of a long and thin object, such as a pipette tip, a temperature sensor, an optical fiber or a pH probe in a Cartesian or also in a polar system of coordinates.

Publication WO 2007/071613 A1 furthermore discloses a device for the conditioning of a system liquid for a liquid handling system, in which the following prior art is cited. Branches of industry that deal, for example, with biochemical techniques in pharmaceutical research or clinical diagnostics require systems for the processing of liquid volumes and liquid samples. Automated systems usually include a liquid handling device, such as a single pipetting device or several pipetting devices which are used at liquid containers that are situated on the work table of a work station or a so-called "liquid handling workstation". Such work stations are often able to carry out the most diverse of chores on these liquid samples, such as optical measurements, pipetting, washing, centrifuging, incubation and filtration. One or more robots, which now operate by Cartesian or polar coordinates, can be used for the sample processing at such a work station. Such robots can carry and relocate liquid containers, such as test tubes or microtitration plates. Such robots can also be used as so-called "Robotic Sample Processor" (RSP), for example, a pipetting device for aspirating and dispensing, or dispensers for distributing the liquid samples. Preferably, such systems are guided and controlled by a computer. One decisive advantage of such systems is that large numbers of liquid samples can be processed automatically over lengthy periods of hours and days, without a human technician having to be involved in the process. Such systems can automatically process entire series of tests. Such series of tests, like the so-called "ELISA tests" (Enzyme-Linked Immuno Sorbent Assay) are now indispensable in present day clinical diagnostics and life science research. Two processes need to be basically distinguished from each other for automation in liquid handling: the defined taking up (aspiration) and the subsequent giving out (dispensing) of liquid samples. Between these processes the pipette tip is usually moved by the experimenter or an automatic machine, so that the place of taking up a liquid sample is different from its place of giving out.

EP 1 206 967 A2 describes a prior art from which it is known that drops with a volume of more than 10 μl can be very easily dispensed from the air, because the drops when properly handled with the pipette leave the pipette tip of themselves. The drop size, then, is determined by the physical properties of the sample liquid, such as surface tension or viscosity. Thus, the drop size limits the resolution of the amount of liquid being dispensed. On the other hand, the taking up and giving out, or pipetting, of liquid samples with a volume of less than 10 μl usually require instruments and techniques that guarantee the dispensing of such small samples. Systems for the separating of samples from a liquid are known as automatic pipetters. Such systems serve, e.g., to dispense liquids into the receiving wells of standard microtitration plates (commercial brand of Beckman Coulter, Inc., 4300 N. Harbour Blvd., P.O. Box 3100 Fullerton, Calif., USA 92834) or microtitration plates with 96 wells. Reduction of specimen volume (e.g., for filling of highly dense microtitration plates with 384, 864, 1536 or even more wells) is playing an increasingly important role, and great significance attaches to the accuracy of the sample volume given out. Increasing the number of samples usually also entails a miniaturization of the experiment, so that the use of an automatic pipetter becomes indispensable and special requirements need to be placed on the accuracy of sample volume, as well as the goal-seeking ability or dispensing of this automatic pipetter. More simple automatic pipetters, so-called "open systems", connect the reservoir vessel for the liquid being pipetted to the pipette tip by a line, in which a dispenser pump can be installed. Dispenser pumps are usually designed as piston pumps. To take up (aspirate) the sample, the pump alone is placed in operation, and the pipette tip merely passes on the flow of liquid in passive manner. To give out or dispense a sample volume, the pump is then shut off or bypassed. A pipette tip in the form of a microejection pump, for example, is known from EP 0 725 267 A2, and it is used to actively separate a liquid sample. The liquid is delivered further by the hydrostatic pressure prevailing in the line between reservoir vessel and pipette tip.

In the current prior art, such as is known for example from publications WO 2006/000115 A1, WO 02/059626 A1 and EP 1 477 815 A1, it is customary to fill and wash and supply reagent to all eight wells or positions of a microtitration plate with eight equidistantly arranged hollow needles at the same time. Or, according to another prior art, these microtitration plates are filled in succession with a single hollow needle and likewise washed and aspirated in succession. This method has the drawback that, due to the filling in succession, time differences can very well occur, so that a time difference of 10 s or more can very well occur between the incubation/reaction time in the first well (reaction space) and that in the last well. This also leads to differing results. In particular, this also holds when the wells are dried for different lengths of time after the aspiration and before being filled with reagent.

SUMMARY OF THE INVENTION

Therefore, the problem on which the invention is based is to avoid these drawbacks of the prior art. The invention also has the goal of making possible a testing usually with only single wells of the microtitration plates prepared in this way. Since several wells are for the most part used in parallel in the prior art, this leads to an increased consumption of costly reagents.

Now, this problem is solved according to the invention by the device for the study of biological or chemical samples by means of a reagent liquid supplied via a pipette and a cleaning liquid supplied and removed via a pipette.

This is accomplished in that three separately controlled hollow needles are arranged close alongside each other in such a way that all three of them come to stand at the same time above a single well or cup and then the middle needle preferably fills in the reagent. After a reaction time or incubation time, the other two outer needles then become active, i.e., the solution is aspirated by means of a second needle and provided with a washing solution by means of a third needle, after which aspiration is done again with the second needle. However, for the duration of an entire reaction cycle, the hollow needles themselves do not move across the well and all reactions or washing steps occur with no movement steps taking place between them and possibly wasting time. One hollow needle, preferably the middle one carrying the reagent, is movably mounted, and it moves up and down during the filling by means of a motorized mechanism. Such a mechanism can be a gear mechanism, a spindle mechanism, or also a chain or V-belt drive. In the bottom part, all three needles are held in a cylindrical guide part, having a separate opening for each needle.

The arrangement of the individual hollow needles is also preferably such that no contamination occurs. This is accomplished in that the washing needle is situated somewhat above the aspiration needle, so that it does not dip into the reagent itself. The special arrangement of three parallel needles makes it possible to place them together in a recess of the microtitration plate.

Another essential feature of the invention is that the needle unit is supported by means of magnets. This has the advantage that, if the system fails or, for example, if the hollow needles strike against a reagent vial left inadvertently inside the analysis device, the needles will not get bent or the vial will not be spilled, but rather the needle unit will be released from its magnetic support and will drop out. This triggers an additional stopping mechanism, so that no damage can result from this. Thanks to a special support, the needle unit is well protected against damage. Thus, the hollow needles cannot get bent or broken if they are inadvertently set down on surfaces, since the needle unit will first be moved out of its position. The user can then easily secure the needle unit again with its three hollow needles.

Two hollow needles are in a fixed position: the dispensing needle and the aspirating needle. The third needle is responsible for supplying the reagent and can enable the taking up or giving out of reagent through motorized actuation, by means of level detection. As a result, the supplying of reagent can be very fast.

The reagents themselves are supplied by means of a microsyringe system operating similar to the prior art, which is preferably introduced into the particular sample needle via a two-way valve by means of a thin microscopic tube system. These microsyringes are not screwed on in tedious fashion, as in the prior art, but rather held in position by means of a magnet, which on the one hand enables an easy and quick replacement with no problem, and on the other hand triggers the above-described stopping mechanism in event of malfunction. The entire needle system is arranged above a circular rotatable work platform, on which is located preferably a series of reagents, a series of serums, a dilution series and microtitration plates, and it can thus reach any given spot within the circular work platform. The needle system is moved back and forth, by means of a robot chain, for example, or it is moved radially back and forth via a spindle drive by the turning of a threaded shaft. In the lower region of the needle system is arranged a peristaltic pump, likewise supported by means of a magnet, which preferably pumps the washing liquid into the hollow needles.

The magnet support of the needle unit is also designed so that the outer ones are fastened to a support plate and the middle one can slide up and down in a guide groove. The magnets are arranged at the side and press the support plate against a stationary abutment. The other magnetic fasteners, such as for the microsyringes and the peristaltic pump part, are arranged flush at the top.

The ring, also arranged on the outside, has regions which basically contain the reagent vials for making the dilution series. Another region of the ring is reserved for patient serums, and there is a third for the reagents. In one preferred embodiment, yet another ring is arranged between the microtitration plates located in the middle, in which are arranged fluorescence reagent vials (also known as slides). These slides can likewise be loaded by means of this device with needle system and then be read off at a later time by a technician specializing in this. Incidentally, the same holds for the microtitration plates, since the analysis device itself has no elements for evaluating the individual cavities or wells. Hence, this is a kind of semiautomatic unit. In a preferred embodiment, the analysis device has a barcode reading unit in its rear part. The individual serums withdrawn by a physician are provided with the patient's barcode. The analysis device links the data by means of a software program and can then determine at once which test or which experiment or which serum needs to be loaded with which reagents. In this way, it is possible to test for different diseases in one or more patients at the same time.

The barcode reader is also used to identify the individual circular reagent vial stands (also known as "racks"). As a matter of fact, different clients use reagent vials of different thickness and so the analysis device can recognize whether it involves a rack with a few thick reagent vials or a rack with a lot of thin reagent vials lying close to each other and thereby appropriately steer the rotation of the rack near the sampling location. The racks are also held in their anchoring by means of magnets (in addition to openings in the bottom part). At the back side of the device are arranged connection devices for bottles or catching containers for the aspirated liquids, as well as connection options for washing solutions etc. At the back side of the analysis device there is a port for a data processing system or a personal computer (PC), especially a USB interface. The entire analysis device is operated by means of a 24 Volt system, that is, an appropriate transformer is mounted outside of the device.

Furthermore, the analysis device contains a detection unit, which indicates whenever a reagent is used up or a reagent vial becomes empty. The PC notices the location of the reagent vial, switches on a beacon light which blinks or burns steady, and then rotates the empty bottle directly to the beacon light. Then the user does not have to look for the empty bottle, since he knows it is found at the blinking light.

Furthermore, an indicator is also provided in the analysis device, which indicates various problems by changing color. Thus, for example, it is possible in the case of the already discussed indication of an empty reagent to also indicate what the problem is for the reagent by an appropriate color of the indicator device; for example, there is a malfunction if it is red, the buffer is used up if it is yellow, etc. This can also be applied to the overall lighting of the device, so that when there is a malfunction the various light-emitting diodes present in the device will change color, thereby also indicating the nature of the fault at once.

Since the hose piece of the peristaltic pump is held in position with the magnets, it can be easily replaced by the user. This also makes possible an easy replacement of the interior hose pieces, so that reagent can be supplied quickly after the last washing step.

Thanks to the arrangement of the dispensing needle next to the aspirating needle, it is possible to add reagent directly after the aspiration. This is very advantageous, since other devices need to first take the microtitration plate out of the washing station in order to add reagent. Thanks to this direct adding of reagent it is not possible for the sensitive bottom of the specimen to dry out, thus possibly falsifying the results.

Due to its helmet shape, the analysis device should give the client a feeling of security for the automatic process. Furthermore, an audible (audio) and a visual alarm as well as a direct fault display can be provided in the carrousel. In event of instrument error or operator error, the audio alarm is additionally supported by blinking light-emitting diodes (LEDs). The carrousel automatically drives to the place of the LED indicating the fault, making it possible for the user to quickly correct the fault.

The analysis device of the invention preferably has an independent processor, which is able to control the entire routine of an autoimmunity laboratory and infectious serology laboratory. Its plate capacity preferably holds two microtitration plates. Its slide capacity preferably holds 20 specimen slides, which may also be of different shapes. The minimum sample volume taken up is 1 µl. The minimum sample volume of a test tube is preferably 100 µl for Elisa and 50 µl for IFA. The incubation temperature is preferably 23 to 40 degrees C. The LIS Link corresponds to the ASTM standards. The operating systems Windows 2000, Windows XP and Vista are preferably supported as the computer software. An external 24 Volt power supply is preferably provided for the operation of the analyzer.

Figure 2:
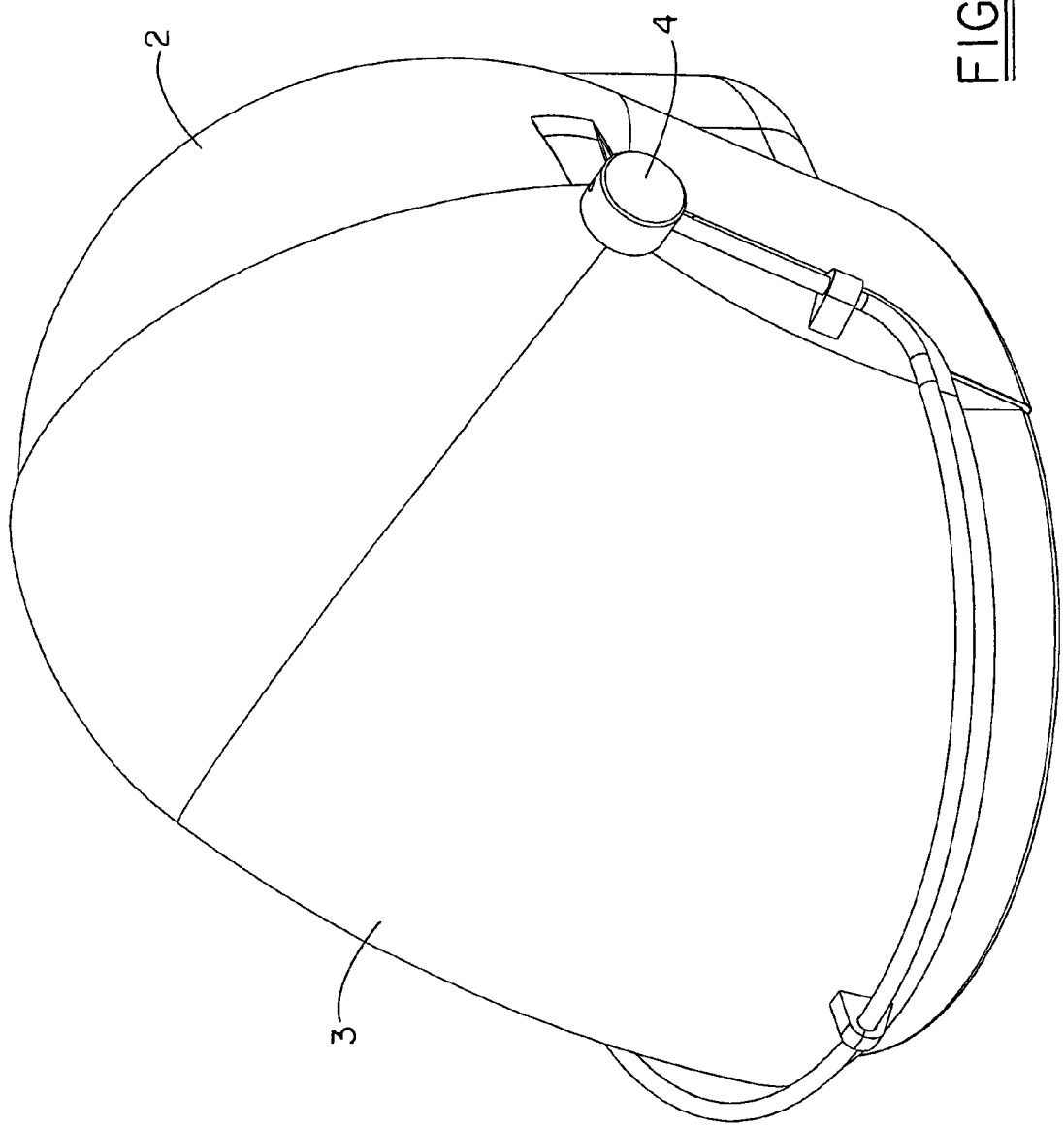
Figure 3:
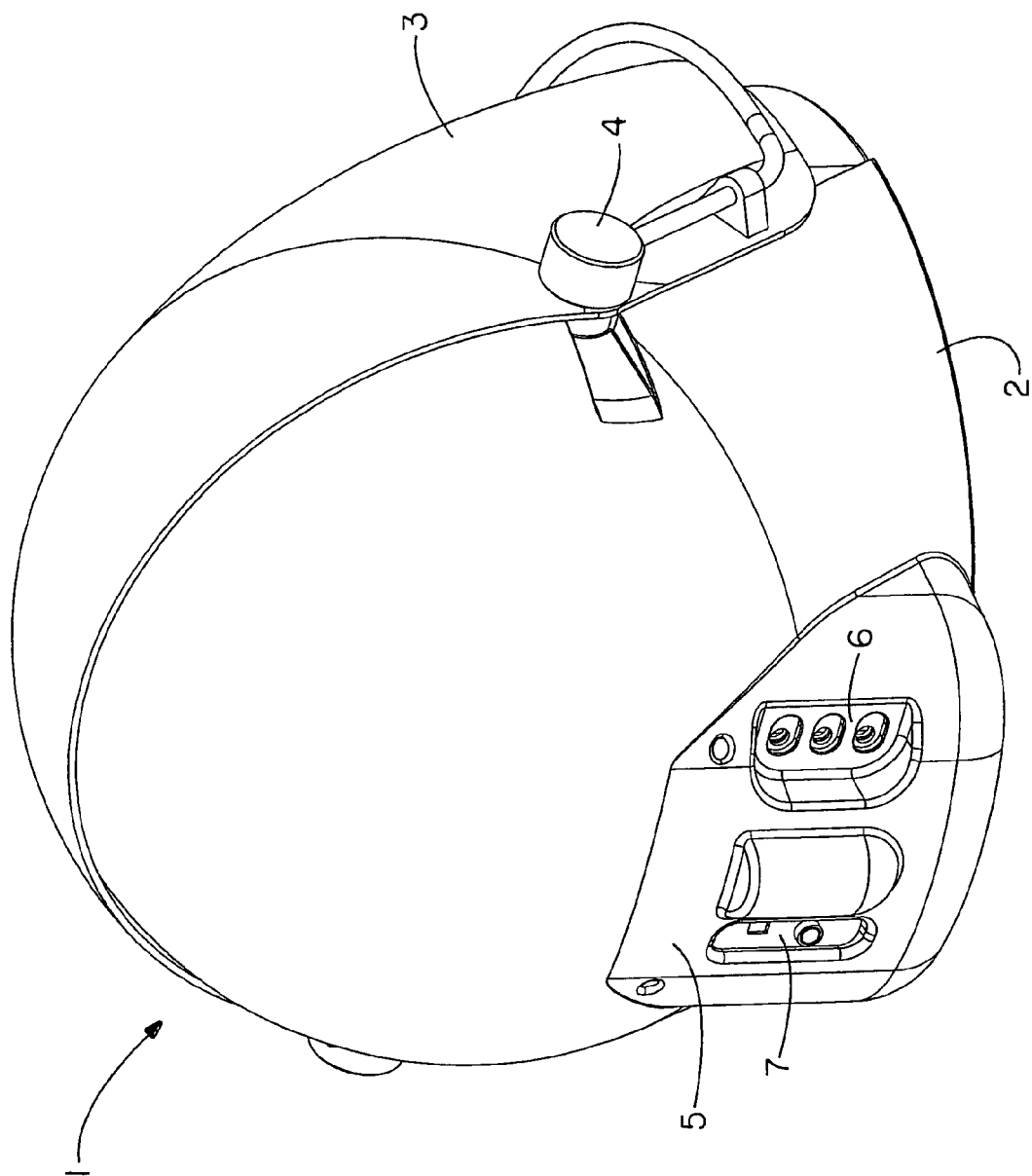
Figure 4:
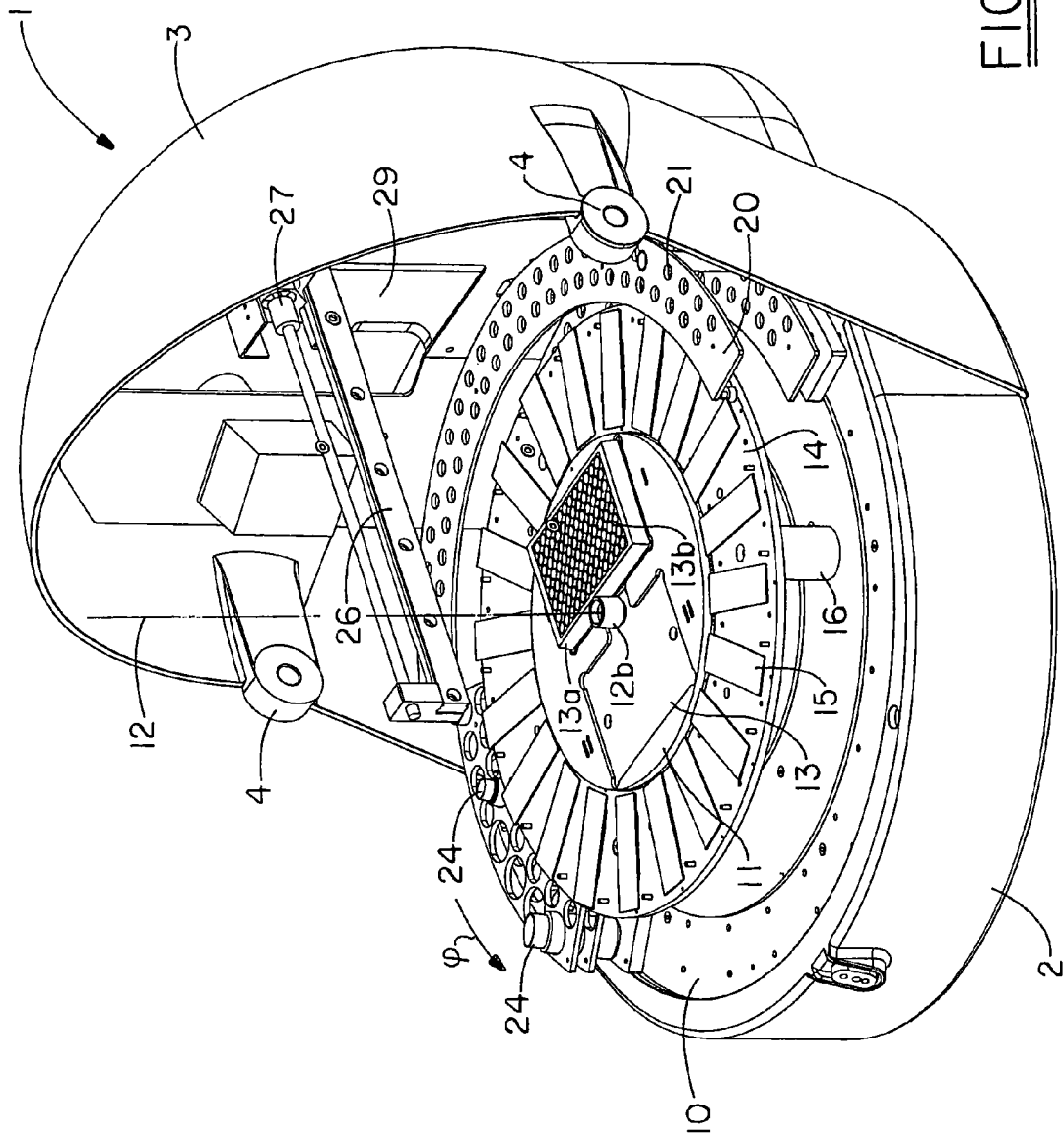
Figure 5:
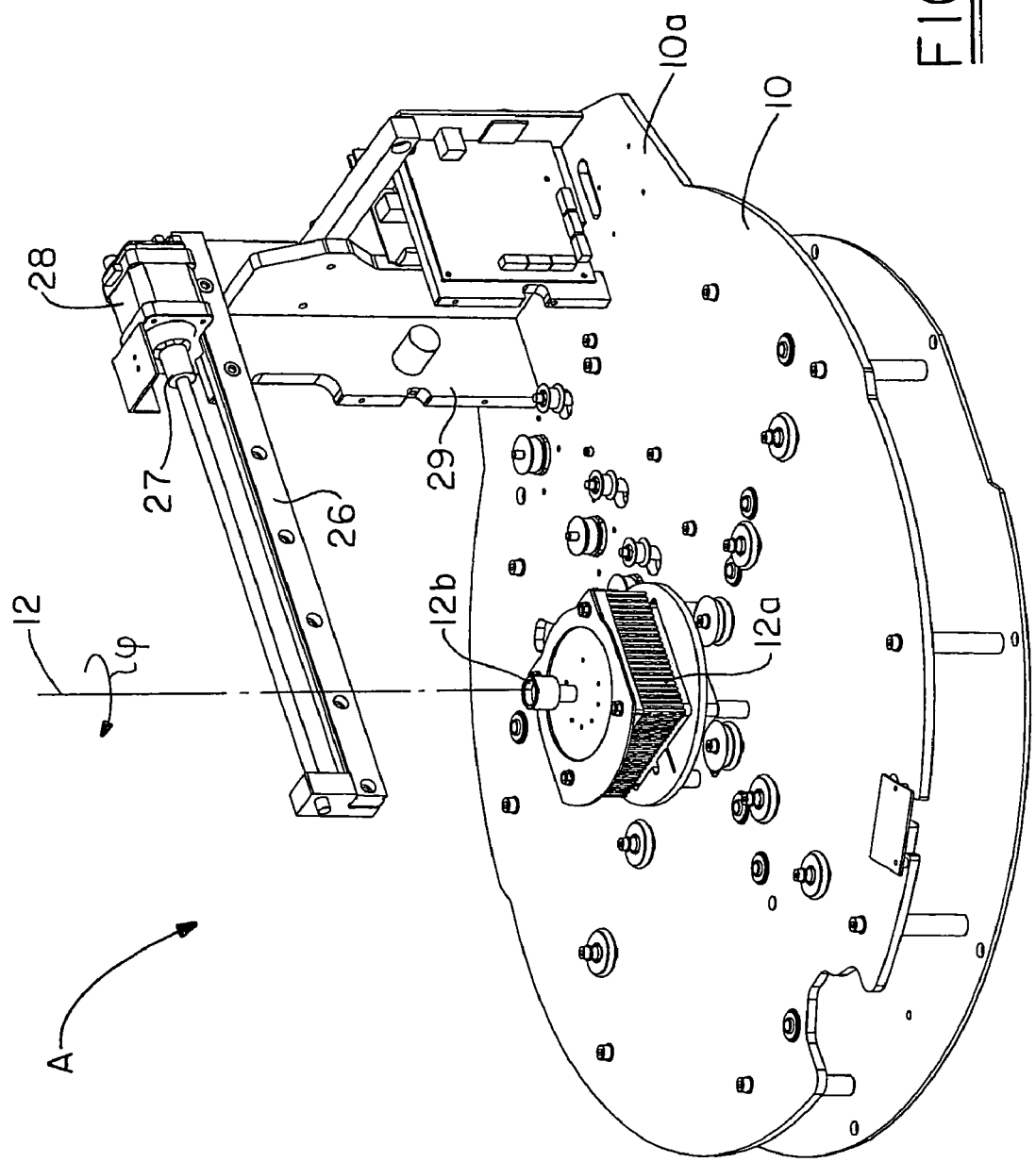
Figure 6:
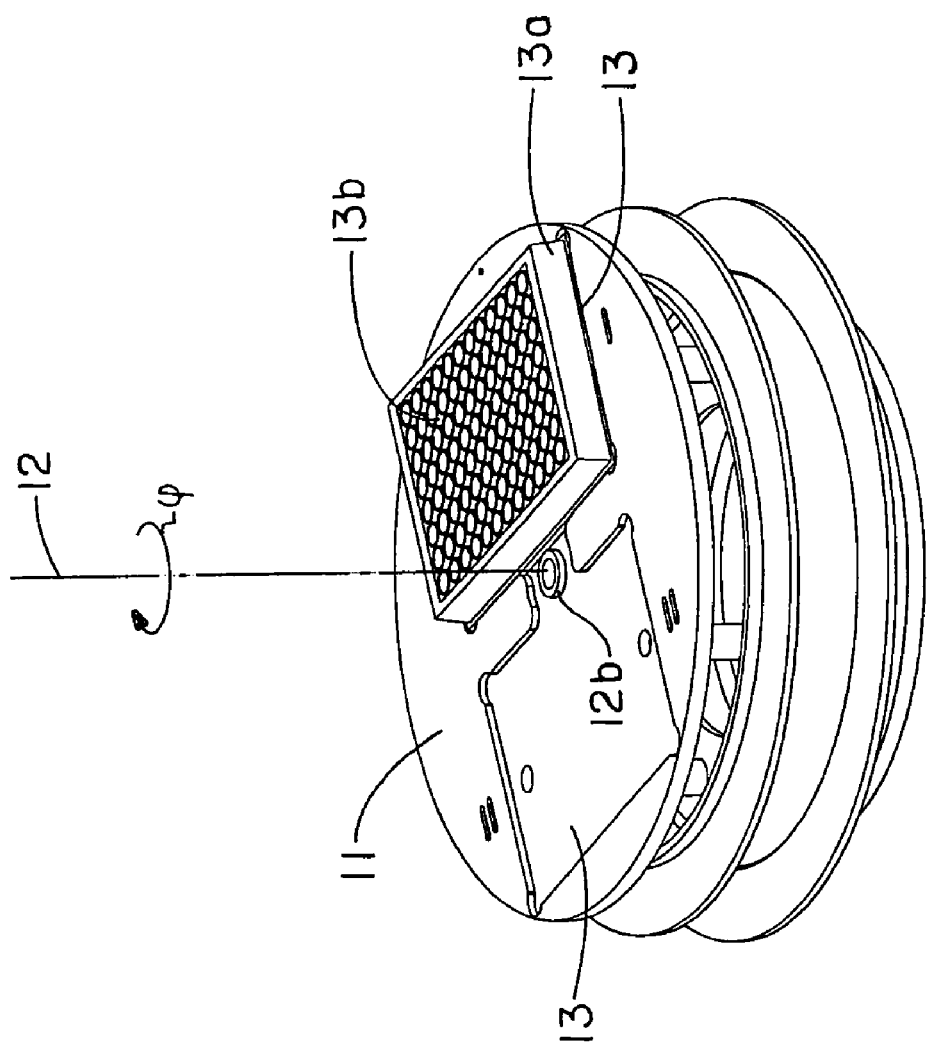
Figure 7:
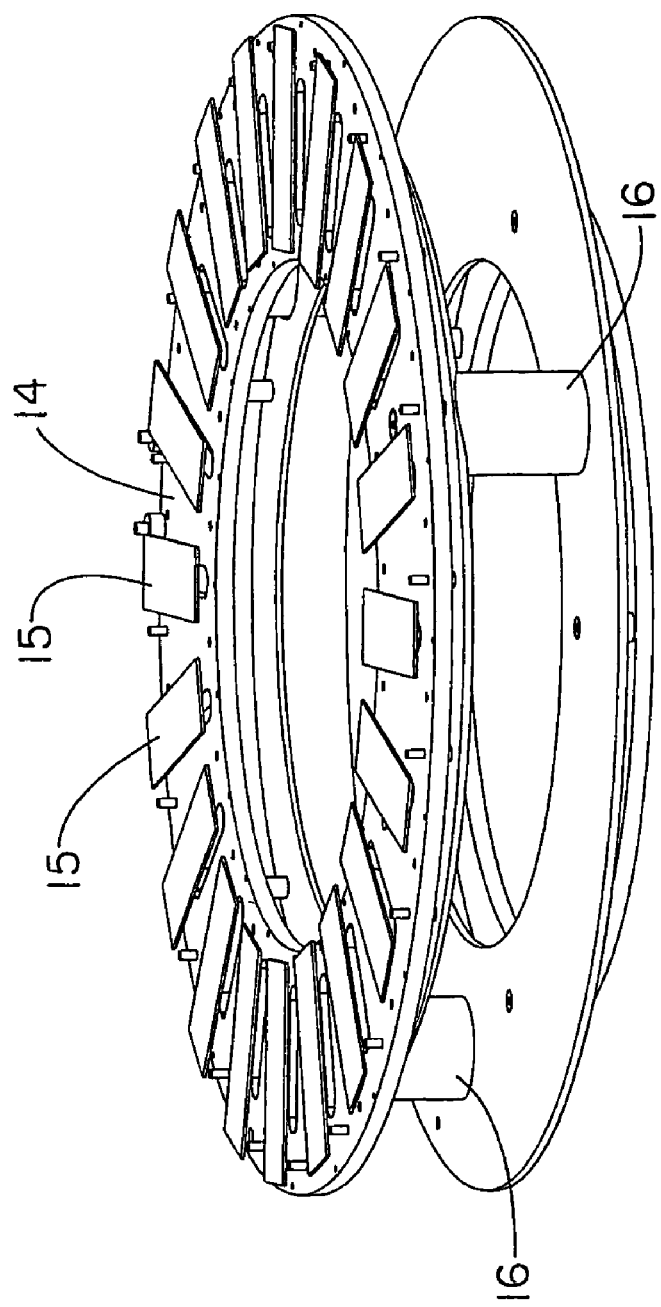
Figure 8:
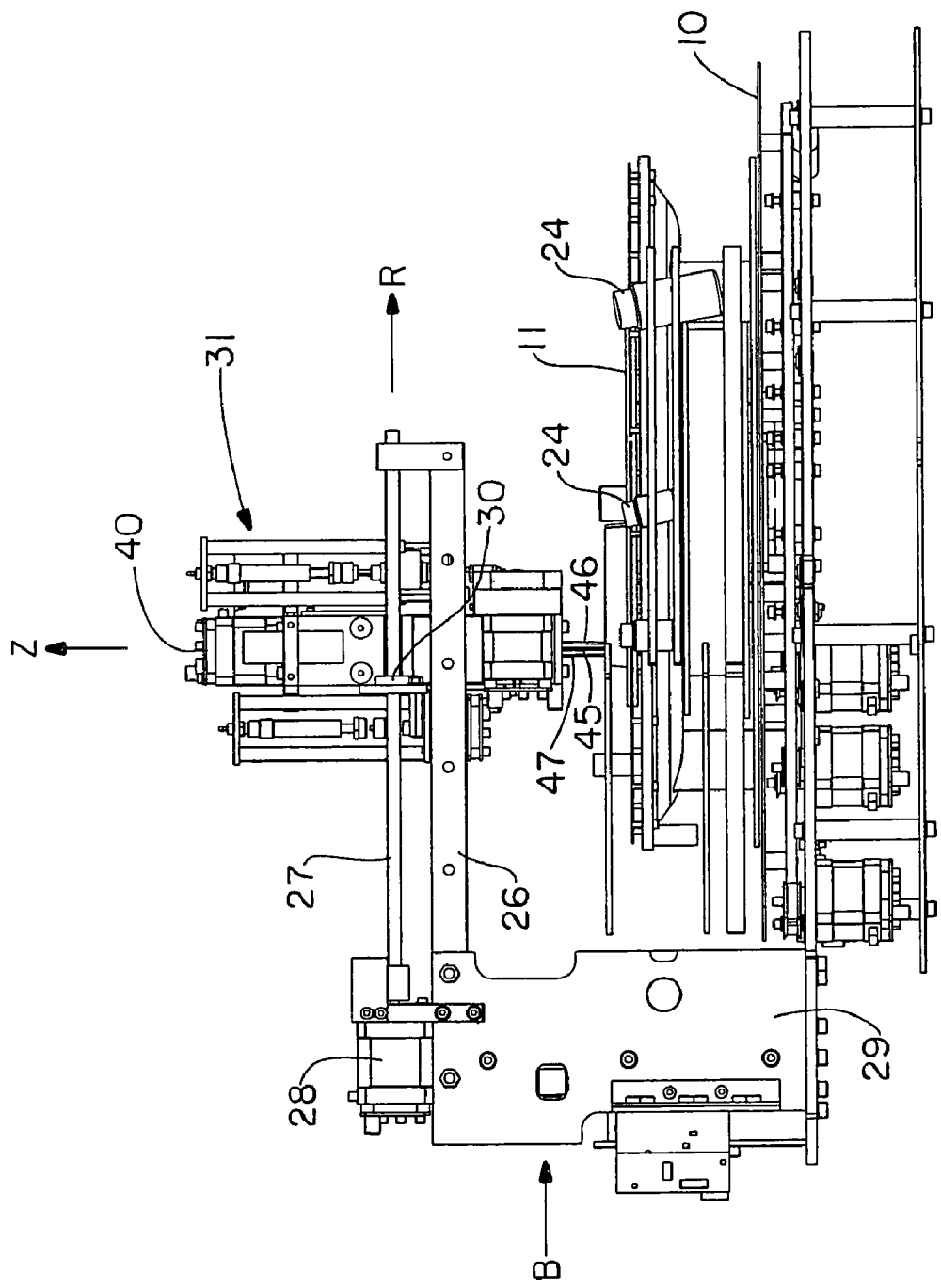
Figure 9:
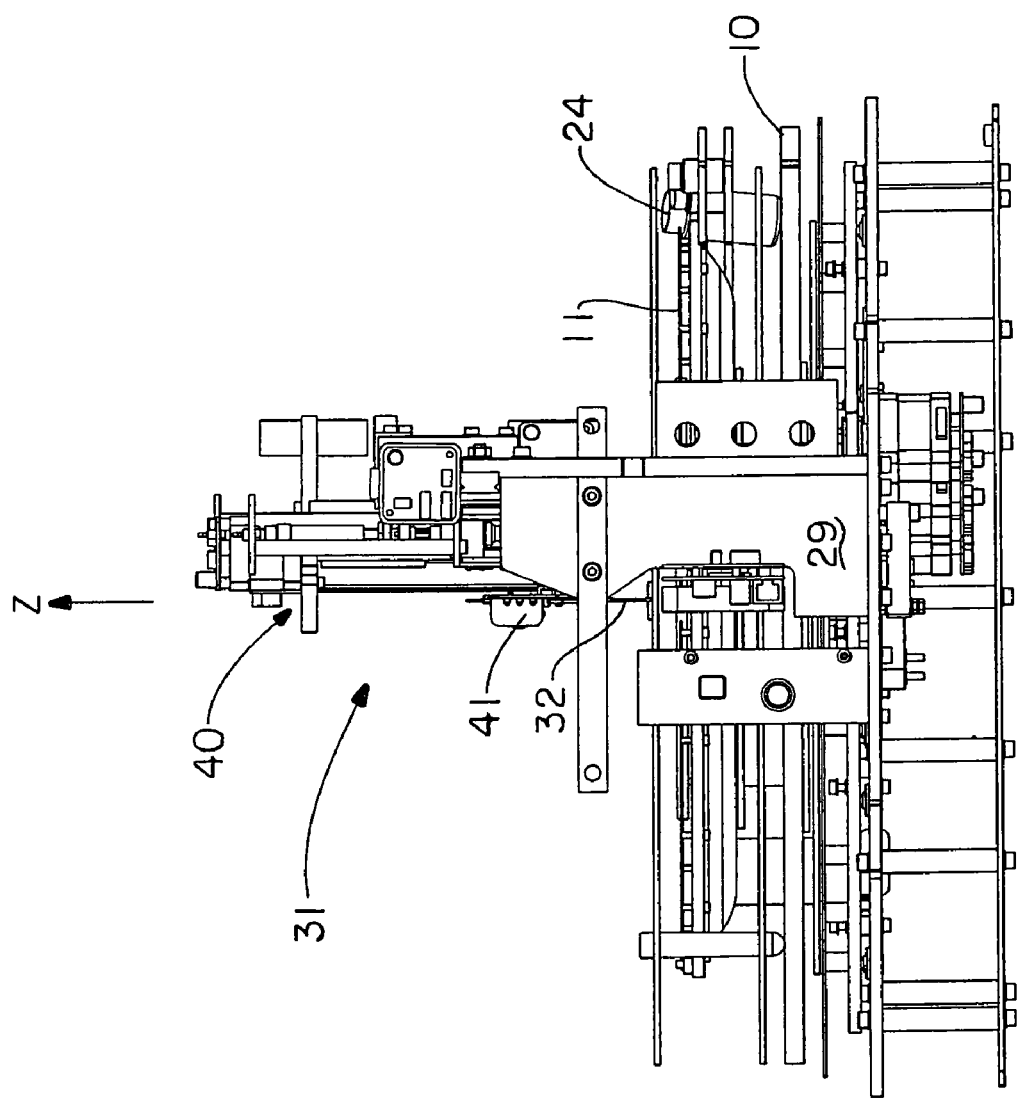
Figure 10:
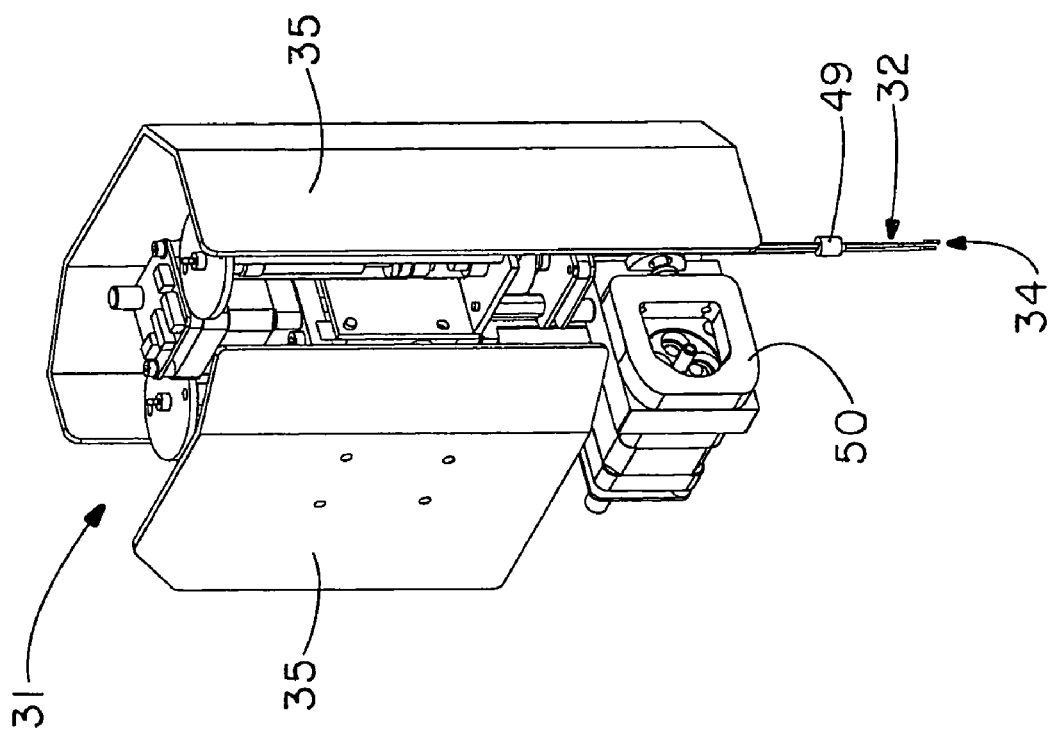
Figure 11:
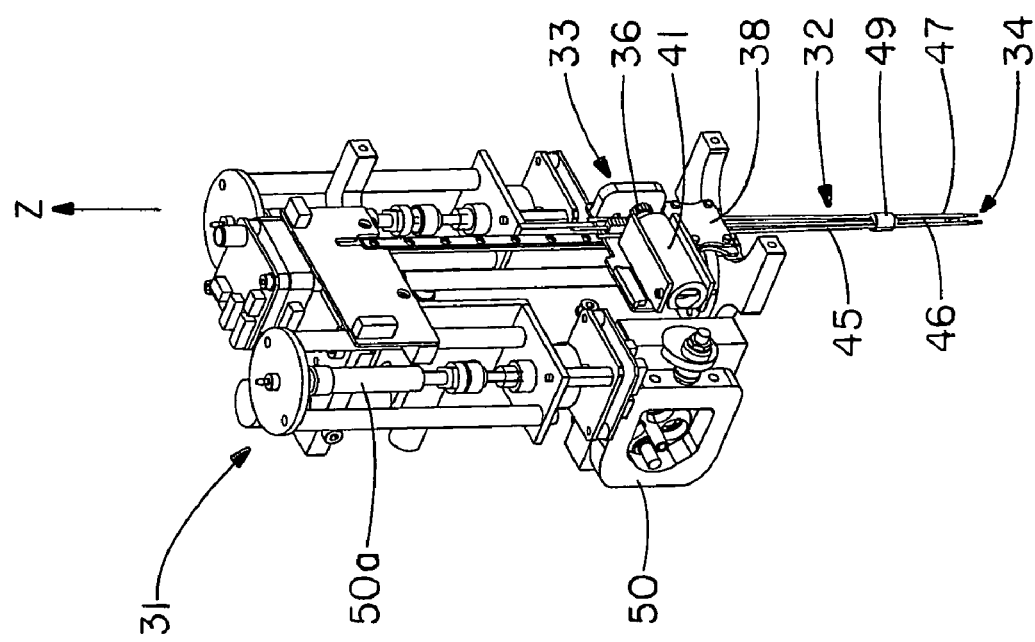
Figure 12:
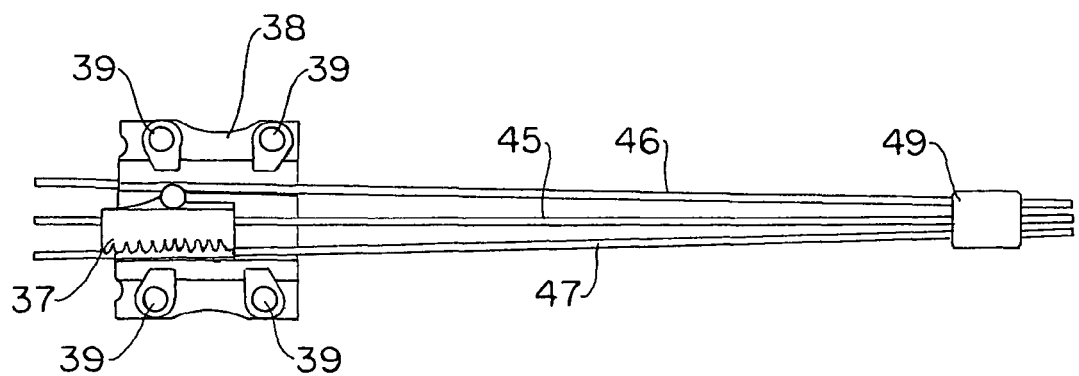
Figure 13:
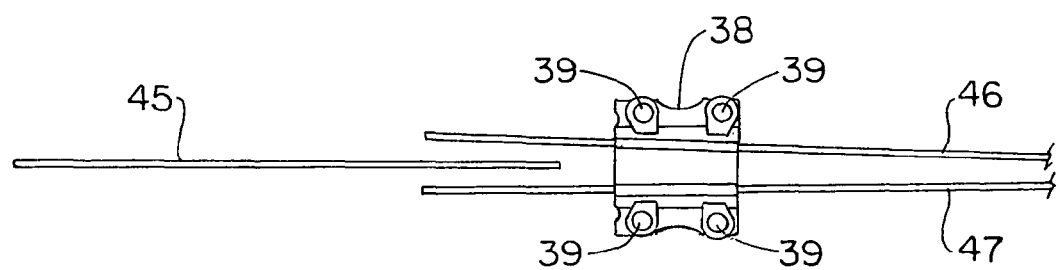
Figure 14A:
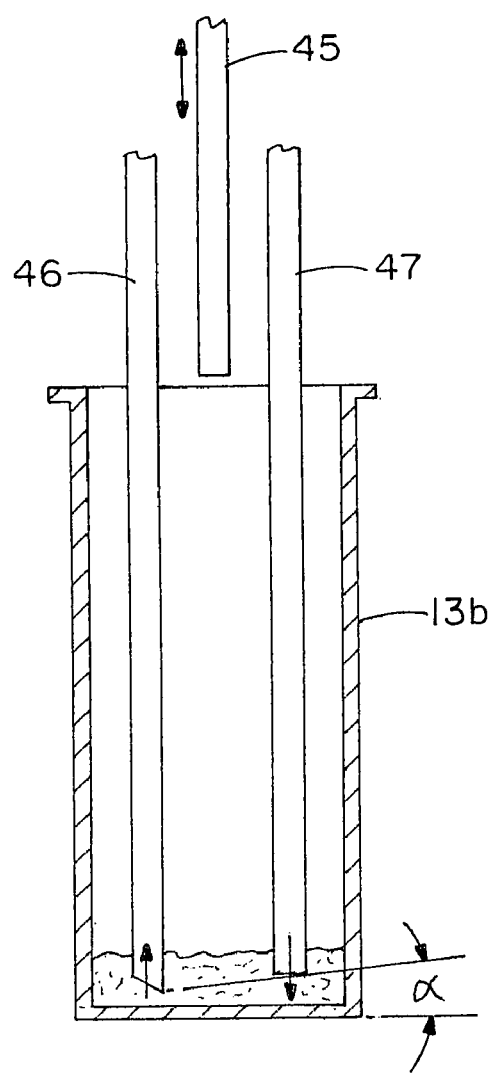
Figure 14B:
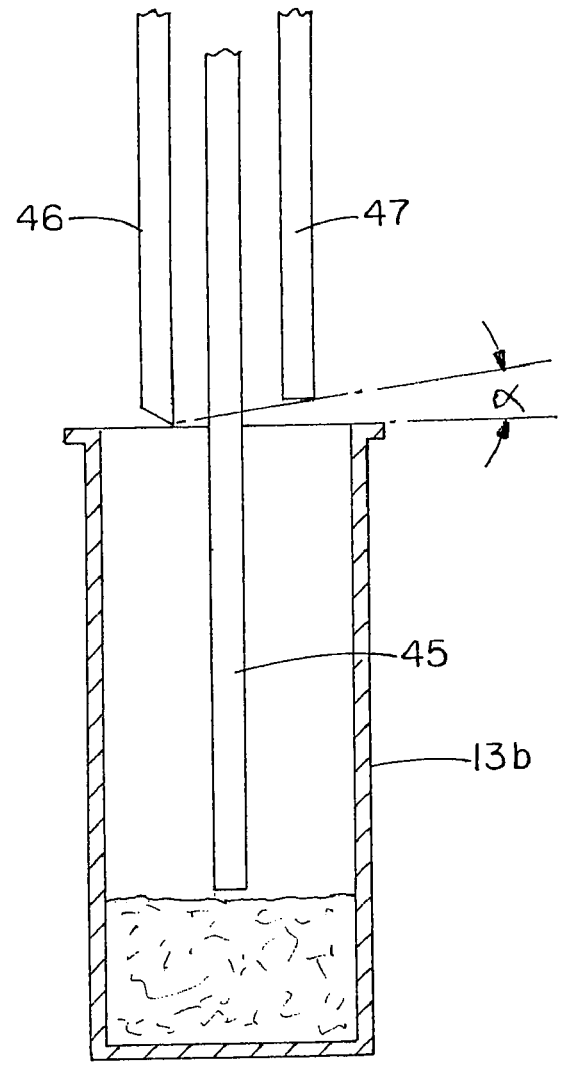

A first sample embodiment of the invented device for the study of biological and chemical samples shall now be explained more closely by means of schematized drawings, not restricting the scope of the invention. The same reference numbers are used in all drawings. These show:

FIG. 1 a perspective overall view of the first embodiment of a device according to the invention for the study of biological and chemical samples with a helmet-shaped instrument housing with a visor-like cover that can be flipped open, FIG. 2 a perspective overall view of the invented device of FIG. 1 with visor-like cover closed, looking on a slant from the front, FIG. 3 a perspective overall view of the invented device of FIG. 1 with visor-like cover closed, but looking on a slant from the rear, FIG. 4 a perspective overall view of the invented device of FIG. 1, but with the vertical needle drive taken out, FIG. 5 a perspective partial view of the invented device of FIG. 1, with the helmet-shaped housing and rotatable working plate removed as compared to the overall view of FIG. 4, FIG. 6 a perspective partial view of the invented device of FIG. 1, where only the rotatable working plate is shown with a microtitration plate placed thereon, FIG. 7 a perspective partial view of the invented device of FIG. 1, showing only an outer reagent support ring, FIG. 8 a side view in direction A of the invented device of FIG. 1, without the helmet-shaped housing and without outer casing of the needle system, beneath which are motors for a ring-shaped working plate, FIG. 9 a rear view in direction B of the side view shown in FIG. 8 of the invented device of FIG. 1, FIG. 10 a perspective view of the needle system with outer casing of the invented device per FIG. 1 with drive for hose pump, FIG. 11 a perspective view of the needle system shown in FIG. 10, but with outer casing removed from the invented device of FIG. 1, FIG. 12 a top view of the holding plate holding the three hollow needles of the needle system shown in FIG. 11, in which the middle needle arranged able to move relative to the other two needles has a toothed rack mounted on it, FIG. 13 a top view of the holding plate holding the three hollow needles of the needle system shown in FIG. 11, in which the middle needle arranged able to move relative to the other two needles has been removed from the holding plate, FIG. 14 two side views of the pipette tips of the three hollow needles of the invented device of FIG. 1, left, in lowered position inside a cup or well during the washing process, and right, in the raised position while delivering reagents, FIG. 15-18, several perspective views of the peristaltic pump and its individual parts of the invented device of FIG. 1.

DETAILED DESCRIPTION OF THE INVENTION

FIG. 1 shows an overall perspective view of an invented device 1 for the study of biological and chemical samples, used as an analysis device. The device 1 has a helmet-shaped instrument housing 2 with a hinged visor-like cover 3, which can be opened and shut by two hinges 4. FIG. 2 shows the shut condition with a slanting view from the front, while FIG. 3 shows the shut condition at a slant from the rear. At the back 5 of the instrument housing 2 are electrical plug strips 6 and 7, where the various plugs for the electrical 24 V mains, the electrical control signals for a data processing system (personal computer), and measurement signals (especially a USB port) are connected.

The instrument housing 1 has a base plate 10, which carries a working plate 11 (also often called a carrousel) situated horizontally when in use, being able to turn about its vertical axis 12 from a motor or drive into a predetermined angle position φ. On this inner working plate 11 there are two rectangular recesses 13 to accommodate two sample holders 13a, only one sample holder 13a being put in place, and containing a plurality of cups or wells 13*b* (as can be better seen in FIG. 6): this inner working plate 11 is enlarged in the radial direction by an annular working plate 14, on which transparent specimen slides 15 are arranged in the radial direction, each of them carrying biological or chemical samples. This annular working plate 14 is secured by means of supports 16 to the base plate 10. This annular working plate 14 can, however, in other configurations not shown, be turned by a separate rotary drive or be turned along with the inner working plate. Radially outward from this annular working plate 14 there is provided a roughly semicircular reagent vial holder 20, which has holes 21 for rather small reagent vials. Furthermore, in the same circumferential region at the left side of FIG. 1 (seen even better in FIG. 4 without the needle system 31) is arranged a roughly circular quadrant-shaped reagent vial holder 22 with larger holes 23 for larger reagent vials 24.

Above the inner working plate 11 is arranged a robot manipulator 25, which carries a support arm 26 extending in a horizontal direction parallel to the inner working plate 11 and a slide 30 (visible only in FIG. 8) which can move along this support arm 26 by means of a horizontal spindle drive 27. This slide 30 carries a needle system 31 which can move in the vertical Z direction with the needle unit 32, which can be brought into predetermined vertical positions by a first vertical drive 33 (seen in FIG. 11). In this way, the free tips 34 of the needle unit 32 can be placed in an upper position above and in a lower position within a cup or well 13*b* of a sample holder 13*a*. The needle system 31 is shown in FIG. 1 with an outer casing 35.

FIG. 5 better shows the spindle drive 27 of the robot manipulator 25 and the rotary drive 12*a* as compared to FIG. 4, thanks to removing the helmet-shaped instrument housing 2, the inner working plate 11, the annular working plate 14 (often called a carrousel), and the reagent vial holders 20 and 22. The inner working plate 11 has a cleaning or washing unit 12*b* for cleaning the hollow needles, which is fastened via the cooling device 12*a* (only shown in FIG. 5). The spindle drive 27 is driven by a second drive or motor 28. The rear edge region 10*a* of the base plate 10 carries a column 29, which in turn carries the horizontal support arm 26.

FIG. 6 shows a perspective partial view of the inner rotatable working plate 11 with the two rectangular recesses 13 to accommodate two sample holders 13*a*. However, only one sample holder 13*a* is shown, for better clarity.

FIG. 7 shows the annular working plate 14, on which are arranged transparent specimen slides 15 in the circumferential direction. Each of these specimen slides 15 carries samples or reagents, not shown.

FIG. 8 shows a side view in direction A of the device 1 of FIG. 1, where for better clarity the helmet-shaped instrument housing 2 and the outer casing 35 of the needle system 31 have been omitted. This make clear the above described layout of the support arm 26 with the column 29 above the base plate 10. In particular, the needle system 31 with the needle unit 32 is fastened on the support arm 26, and is able to move essentially in the radial direction R by the second electric motor 28 via the spindle drive 27 and the slide 30.

In the upper region of the needle system 31 there is a third electric motor 40, which forms the first vertical drive and which can position the entire needle system 31 in the vertical direction Z via a drive, e.g., a threaded spindle or gear. This is also quite conspicuous from FIG. 9, which shows a rear view in the direction of arrow B of the device shown in FIG. 8. In addition, FIG. 9 shows a fourth electric motor 41, which can move the middle hollow needle 45 in the vertical direction Z relative to the two side needles 46 and 47.

FIG. 10 shows an enlarged perspective view of the needle system 31 with its outer casing 35. The needle unit 32 with the middle hollow needle 45 and the two side needles 46 and 47 sticks out downward. The three needles are held in parallel at very short spacing by a cylindrical guide piece 49 in the projecting region of the needle unit 32. In the lower left part of FIG. 10 is a peristaltic pump (shown on larger scale in FIG. 15), by which liquid can be pumped to a hollow needle through a supply hose, not shown.

FIG. 11 shows a perspective representation of the needle system 31 of FIG. 10 on the same magnified scale, but without the outer casing 35 and from a viewing angle turned around 90 degrees to the right. This shows best the function of the needle system 31. The fourth electric motor 41 as part of the vertical drive 33 moves the middle needle 45 in the vertical direction Z relative to the two side needles 46 and 47 by small gears 36 and a rack 37 fastened to this middle needle 45 (concealed behind the support plate 38 in FIG. 11, but shown enlarged in FIG. 12). In this way, the middle needle 45 is brought into its upper position 55 as depicted, so that its lower free tip is moved upward by the difference Δz relative to the free tips 34 of the two side needles 46 and 47. FIG. 11 shows at bottom left the peristaltic pump 50 from FIG. 10 with a corresponding glass syringe 50*a*.

FIG. 12 shows a top view of a removed needle unit 32 on magnified scale, in which the support plate 38 lies with its outer side at the background of the drawing. The two side needles 46 and 47 are secured in the support plate 38, while the middle needle 45 with its rack 37 is mounted on the support plate 38 to move freely. The support plate 38 carries on each side two annular magnets 39, which form a removable connection with the counter plate arranged on the needle system 31. Thanks to this removable connection, the magnets 39 release the support plate 38 whenever the needle unit 32 accidentally strikes against a foreign object within its range of motion in the instrument housing, so that the support plate with the needle unit 32 fastened to it can drop down onto the working plate 11.

FIG. 13 shows the same top view of the support plate 38 as in FIG. 12, but for better visibility the middle needle 45 is pulled out from the support plate 38.

FIG. 14 shows two side views of the tips 34 of the three hollow needles 45, 46, 47, the left side view showing the three hollow needles 45, 46, 47 each in the fully lowered position within a cup or well 13*b*, while the right side view [shows] the two side needles 46 and 47 in a common upper position and the middle needle 45 within a cup or well 13*b* somewhat above the sample level. The tips of the two side needles 46 and 47 lie in the left side view on a line forming an acute angle α of preferably 1 to 5 degrees with the horizontal plane. Delivery of cleaning liquid occurs due to the higher situated tip of the right side needle 47 and aspiration of the dirty liquid after cleaning occurs via the lowest situated tip of the left side needle. As shown, the middle needle 45 can be moved vertically upward relative to the two side needles 46, 47 by its vertical drive system 33. The left side view shows the situation in which rinsing is done. Here, the middle needle 45 is above the liquid. The right needle 47 (with a straight downward aperture) supplies the washing liquid, while the left needle 46 (with a slanting aperture) aspirates the liquid once again. In the right side view, the filling with reagent is shown, for which the entire needle system 31 is raised and the middle needle 45 is moved downward by means of the already described first vertical drive 33, whereupon the reagent is squirted in. Since, in this condition, the two outer needles are above the well, they cannot contaminate the reagent liquid.

Figure 16:
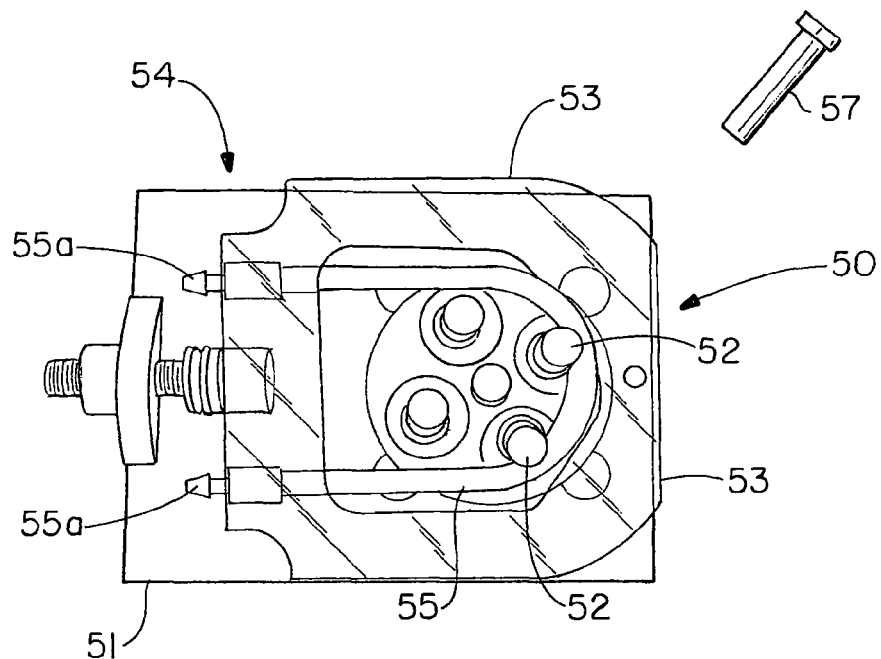
Figure 15:
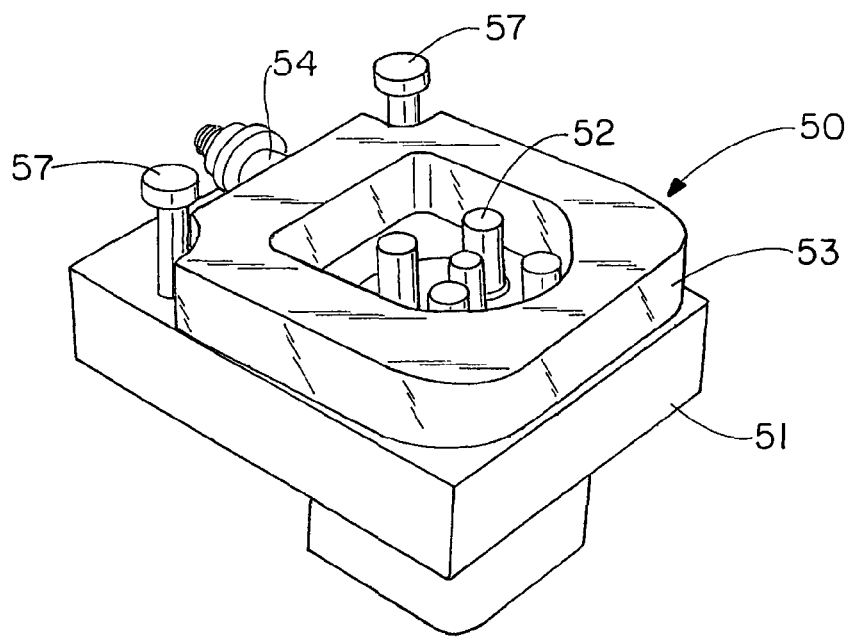
Figure 18A:
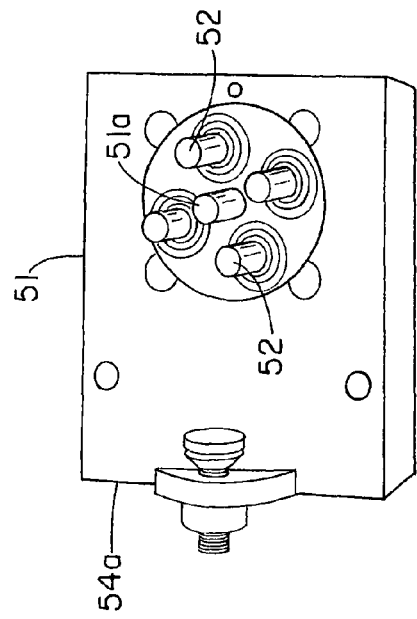
Figure 18B:
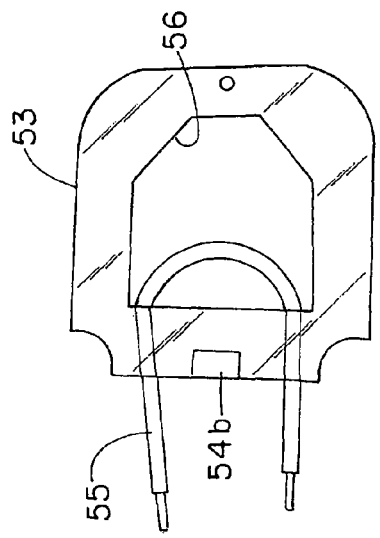
Figure 17A:
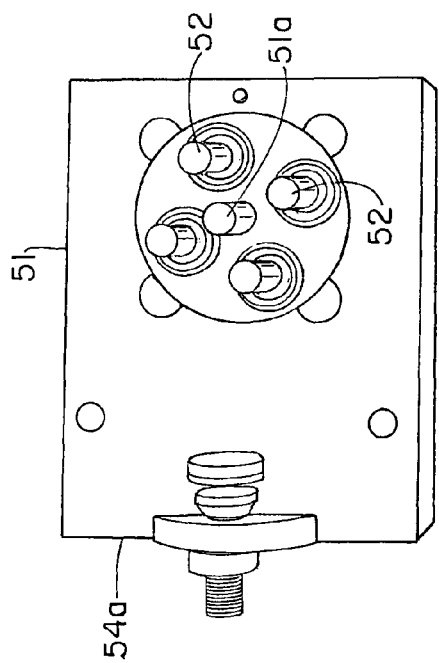
Figure 17B:
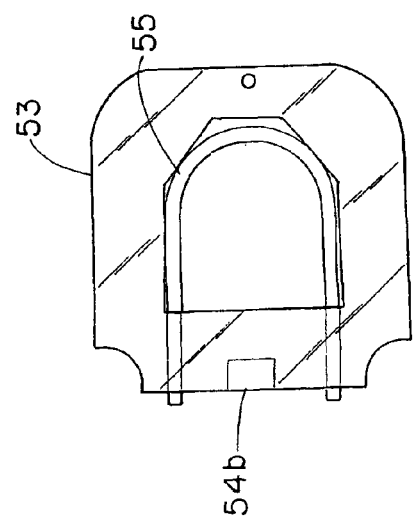

FIG. 15 shows a greatly enlarged perspective view of the peristaltic pump 50 shown in FIGS. 10 and 11, while FIG. 16 basically shows a top view of this peristaltic pump 50 and FIGS. 17 and 18 show the individual parts better. The peristaltic pump 50 consists of a drive part 51 with the four pressing rollers 52 able to rotate about a central axis 51a and the hose part 53, which is fastened by means of a magnet 54 arranged at the left in FIG. 16 with its two magnet parts 54a and 54b, so that the hose part 53 can be loosened by a handle, the drive part and be replaced. The transparent hose part 53, made from acrylic, has a hose piece 55 and several interior abutments 56, while the hose piece 55 is pressed by the rotating pressing rollers 51b against the cooperating abutments 56, so that the liquid present in the hose piece 55 is pumped in the direction of rotation. As can be seen from FIG. 17, the hose piece 55 itself and its coupling pieces 57, shoved onto the ends 55a of the hose piece, can also be easily replaced. When installed in the needle system, these produce the hose connection to the supply hoses.

The representation of FIG. 17 (the magnet part 54b can be seen at left) shows that the connections can easily be pulled out from the transparent hose piece 55 of the peristaltic pump 50, and then the coupling pieces 57 and the hose piece 53 can be separated from the removable hose part 53. In this way, the hose piece 55 can be removed quickly and easily and when changing reagents it can be quickly replaced by a new hose without losing time. Another reason for changing the hose piece 53 is wear and tear, which is relatively great for peristaltic pumps. Since the hose part 53 of the peristaltic pump 50 is held in position with the magnet parts 54a and 54b, it can thus be easily replaced by the user. This also makes possible an easy changing of the hose pieces 55 on the inside.

In a second embodiment of the invention, not shown, the working plate 11 cannot rotate as in the first embodiment. The cups or wells 13b of the sample holder 13a are arranged in a line, coinciding with the horizontal direction (X or Y direction) of the robot manipulator 25, so that it can position the needle system in each cup or well 13b arranged in this line.

In a third embodiment of the invention, not shown, the working plate 11 again cannot rotate as in the first embodiment, but the robot manipulator 25 can be positioned in both the X and the Y direction by means of two horizontal drives. Thus, all samples on a non-stationary two-dimensional working plate 11 can be reached.

What is claimed is:

1. A device for the study of biological or chemical samples by means of a reagent liquid supplied via a pipette or cleaning liquid supplied and removed by means of a pipette, said device comprising:
   an instrument housing with a base plate,
   a working plate arranged on the base plate horizontally in a position of use, to receive the samples in a sample holder having several cups or wells,
   a robot manipulator arranged above the working plate in the position to receive the samples, which carries a support arm extending in a horizontal direction above the working plate and a slide which can move along this support arm by means of a horizontal drive, and
   a system of hollow needles able to move in the vertical direction (Z) on the slide, which carries the pipettes and which can be brought by a first vertical drive into predetermined vertical positions, so that the tips of the hollow needles can be placed in an upper position above and in a lower position within a cup or well of a sample holder, wherein
   the needle system carries three hollow needles forming the pipettes and essentially parallel to each other at a slight spacing in a support plate, whose upper ends are connected via a supply line to an assigned reservoir container,
   one of the hollow needles is arranged so that it can move vertically relative to the other hollow needles in the needle system, and it can be raised and lowered by a given value in the vertical direction by a second vertical drive, and
   the horizontal spacing of the three hollow needles from each other is chosen so small that all three needles can be positioned with their respective tips inside the same cup or well.

2. The device of claim 1, wherein the working plate is mounted on the base plate so that it can turn about its axis, arranged perpendicular to it, and the working plate can turn by a rotary drive to a predetermined angular position ($\phi$).

3. The device of claim 2, wherein the support arm of the robot manipulator extending in the horizontal direction is arranged so that the pipettes can be moved back and forth by the horizontal drive of the slide in the radial direction (R) toward the axis of rotation of the working plate.

4. The device of claim 1, wherein the horizontal drive, the first vertical drive and/or the second vertical drive and/or the rotational drive are each actuated via a motorized drive of a controller.

5. The device of claim 1, wherein the horizontal drive and/or the first vertical drive and/or the second vertical drive are actuated via a spindle drive of a controller.

6. The device of claim 1, wherein
   the three hollow needles are arranged in a common vertical plane (Z) and
   the middle one of the three hollow needles is a hollow needle that is arranged so that it can move vertically relative to one of the outer needles in the needle system.

7. The device of claim 1, wherein a line joining the tips of two hollow needles in the respective lower position inside a cup or well makes an acute angle $\alpha$, wherein $\alpha$ is 1 to 5 degrees, with the horizontal plane, and the dispensing of cleaning fluid occurs through the higher situated hollow needle tip and the aspiration of dirty liquid through the lower situated hollow needle tip.

8. The device of claim 7, wherein the one tip of the one hollow needle which can move vertically with respect to one of the other hollow needles comes to lie between the respective lower and the respective upper position of the other two hollow needles in its respective lower position within a cup or well, and the reagent liquid is delivered via the tip of the hollow needle which can move vertically with respect to one of the other hollow needles.

9. The device of claim 1, wherein the support plate carrying the three hollow needles is held by means of a support magnet in the needle system and can be loosened in such a way that the support magnet can release the support plate within its range of motion upon unexpected striking of the hollow needle tips or the hollow needles against an impeding object in the instrument housing, so that the support plate can drop down with the hollow needles onto the working plate.

10. The device of claim 1, including movable supply lines wherein the movable supply lines are configured as hoses and connected between the respective upper ends of each hollow needle with the reservoir container assigned to it via a cock which can be controlled by a controller.

11. The device of claim 1, wherein the transport of liquid into the supply lines configured as hoses occurs by a hose pump.

12. The device of claim 11, wherein the hose pump configured as a peristaltic pump consists of two magnetically coupled and easily removable halves, so that the hose on the inside, through which the liquid is transported between the pressing rollers, actuated by a rotary drive, and the corresponding abutments, can easily be replaced.

13. The device of claim 1, wherein additional samples are arranged in reagent vials or on specimen slides on the base plate, in an outer region of the working plate, which is arranged outside the sample holder containing the cups or wells.

14. The device of claim 3, wherein the additional samples are arranged in reagent vials or on specimen slides on outer radial rings on the working plate, able to turn about its axis of rotation, and the outer rings are each firmly connected to the rotatable working plate or have their own controllable rotary drive.

15. The device of claim 1, wherein the samples are each characterized by a barcode and can be read by corresponding readers.

16. A system for the study of biological or chemical samples by means of a reagent liquid supplied via a pipette or cleaning liquid supplied and removed by means of a pipette, making use of a device according to one of the preceding claims, wherein
   the instrument housing has the shape of a helmet, which has a visor-like cover at one side, which when opened up allows the user to load the working plate with sample holders, and
   in the closed condition of the visor-like cover a studying of the biological and chemical samples arranged on the working plate can run automatically, controlled by a controller.

17. The method for the study of biological or chemical samples by means of a reagent liquid supplied via a pipette, wherein the samples are each held in their sample holders, which are arranged on the working plate of a device according to claim 1, characterized by the following steps:
   the samples are placed in their respective sample holders, in the form of a matrix, on the working plate arranged horizontal in the position of use,
   the needle system with its three hollow needles is positioned via the controller by the horizontal drive at a position above a cup or well being studied in a sample holder,
   the needle system is lowered by the first vertical drive and the second vertical drive so that at first the first hollow needle, which is arranged so that it can move vertically relative to one of the other hollow needles, is lowered into its lower position, in which its tip is located inside the cup or well, while the other two hollow needles are still located above the cup or well,
   then the reagent liquid is delivered to the specimen located therein,
   the first hollow needle is lifted again by the second vertical drive into an upper position far enough above the cup or well,
   then the second and third hollow needles are lowered together with the first vertical drive until their tips are located just above the sample,
   cleaning liquid is distributed over the sample from the pipette tip of the second hollow needle,
   the excess, unused cleaning liquid is aspirated with the third hollow needle (46),
   the needle system is moved back to its upper position by the first vertical drive,
   the sample is checked for a reaction by a light beam, and the reaction is determined by a color change,
   then another sample is studied in the same way in another cup or well.

* * * * *

UNITED STATES PATENT AND TRADEMARK OFFICE
CERTIFICATE OF CORRECTION

PATENT NO.         : 8,142,719 B2
APPLICATION NO.    : 12/291375
DATED              : March 27, 2012
INVENTOR(S)        : Matthias et al.

It is certified that error appears in the above-identified patent and that said Letters Patent is hereby corrected as shown below:

In Column 14, line 27 (Claim 17). After the word needle, the character number "(46)" should be deleted.

Signed and Sealed this
Eighth Day of May, 2012

David J. Kappos
*Director of the United States Patent and Trademark Office*